United States Patent [19]

Rummo et al.

[11] Patent Number: 4,578,488

[45] Date of Patent: Mar. 25, 1986

[54] BISALKYL BIS(TRIALKANOL AMINE)ZIRCONATES AND USE OF SAME AS THICKENING AGENTS FOR AQUEOUS POLYSACCHARIDE SOLUTIONS

[75] Inventors: Gregory J. Rummo, Bronxville; Robert Startup, Bloomingburg, both of N.Y.

[73] Assignee: Kay-Fries, Inc., Stony Point, N.Y.

[21] Appl. No.: 690,384

[22] Filed: Jan. 10, 1985

Related U.S. Application Data

[63] Continuation of Ser. No. 371,022, Apr. 22, 1982, abandoned.

[51] Int. Cl.$^4$ .............................. C07F 7/00; C07F 7/28
[52] U.S. Cl. ................................ 556/56; 252/8.55 R; 252/8.55 C; 252/315.3
[58] Field of Search ........................................ 260/429.3

[56] References Cited

U.S. PATENT DOCUMENTS

| | | | |
|---|---|---|---|
| 2,824,114 | 2/1958 | Bostwick | 260/429.3 |
| 2,824,115 | 2/1958 | Beacham et al. | 260/429.3 X |
| 2,845,445 | 7/1958 | Russell | 260/429.3 X |
| 2,894,966 | 7/1959 | Russell | 260/429.3 X |
| 2,978,347 | 4/1961 | Koehler et al. | 260/429.3 X |
| 4,313,851 | 2/1982 | Barfurth et al. | 260/429 R X |

*Primary Examiner*—Helen M. S. Sneed
*Attorney, Agent, or Firm*—Felfe & Lynch

[57] ABSTRACT

The synthesis and liquid stabilization of bisalkyl bis(trialkanol amine)zirconates and the use of such zirconates as thickeners for fluids used in resource recovery operations, such as by incorporating the product zirconates described herein in drilling muds, consolidation fluids or fracturing fluids, are disclosed.

10 Claims, No Drawings

BISALKYL BIS(TRIALKANOL AMINE)ZIRCONATES AND USE OF SAME AS THICKENING AGENTS FOR AQUEOUS POLYSACCHARIDE SOLUTIONS

This application is a continuation of application Ser. No. 371,022 filed Apr. 22, 1982, now abandoned.

This invention relates to the synthesis and liquid stabilization of bisalkyl bis(trialkanol amine)zirconates and the use of such zirconates as thickeners for fluids used in resource recovery operations, such as by incorporating the product zirconates described herein in drilling muds, consolidation fluids or fracturing fluids.

According to the invention, product zirconates are obtained from tetraalkyl zirconates and amino alcohols at room temperature. The resultant products, when utilized as described herein as thickening agents for fluids used in resource recovery operations, e.g., aqueous solutions of hydroxypropylguar, effect an increase in the viscosity of the fluids.

In U.S. Pat. No. 2,894,966, issued July 14, 1959, Russell notes that aminoalcohol titanates and zirconates have been found useful in various textile and cosmetic applications and in other fields. He teaches that most such compounds may be stable in aqueous media around a neutral pH but that they tend to hydrolyze or decompose at pH's above about 9, and discloses a method of stabilizing such compounds against undesired reactivity by reacting said compounds with polyhydric alcohols, including monosaccharides.

Bostwick, in U.S. Pat. No. 2,824,114, issued Feb. 18, 1958, teaches the reaction of, among other things, triethanolamine and tetrabutyl zirconate to obtain a polymeric product. He also teaches that ortho and condensed ortho esters of zirconium, such as products of the formula $Zr(OR)_4$, where R is an organic radical including alkyl, may be reacted with, inter alia, triethanol amine, to form water-stable chelated amino alcohol esters of zirconium. He suggests that such compounds are useful as surface active agents for pigments, hydrocarbons, waxes and the like.

In U.S. Pat. No. 2,978,347, issued Apr. 4, 1961, Koehler et al. disclose, among other things, the preparation of surface active agents for use as pigment dispersants comprising organo metallic derivatives of zirconium. Among such derivatives are alkyl triethanolamine zirconates, including diethyldi(triethanolamine)zirconate and diisopropyldi(triethanolamine)zirconate. The former is prepared by refluxing tetraethyl zirconate with triethanolamine and the latter by heating a complex of tetraisopropyl zirconate and isopropyl alcohol with triethanolamine. The product compounds are said to be soluble in $CCl_4$, ethanol and water.

Barfurth et al., in U.S. Pat. No. 4,313,851, dated Feb. 2, 1982, disclose the stabilization of a solution comprising diisopropoxy bis(2,4-pentanedionato)titanium with water.

The bisalkyl bis(trialkanol amine)zirconates of the invention are generally of the structure

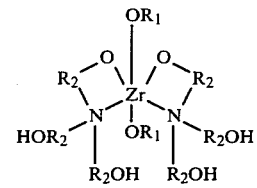

where $R_1$ and $R_2$ may be the same or different and are preferably individually alkyl having from 1 to 8 carbon atoms, including methyl, ethyl, propyl, isopropyl, n-butyl, tert-butyl, sec. butyl and the like up to octyl. Both $R_1$ and $R_2$ are preferred to have from 1 to 5 carbons, $R_1$ is more preferred to have either 3 or 4 carbons, and $R_2$ is more preferred to have either 2 or 3 carbons. The most preferable compounds according to the invention have $R_1$=n-propyl or n-butyl and $R_2$=ethyl.

It has been found that synthesis of these compounds proceeds readily from the admixture of tetraalkyl zirconates and amino alcohols in solution at room temperature. Molar ratios of about 2 to 1 (trialkanol amine:zirconate) may be employed, while the preferred ratios are from about 2 to 1.5 and the most preferred ratio is 2:1.

Although zirconates according to the invention would be utile as solids (e.g., from ease of handling and shipment to point-of-use), the majority of users of resource recovery fluids have equipment and processes geared to the immediate utilization of thickening agents in liquid form. It is therefore preferred to obtain and maintain the products of the invention in liquid form.

We have found that the likelihood of obtaining liquid product is drastically enhanced by using the more pure commercially available forms of reactants. Where, for example, the amino alcohol used is triethanol amine (i.e., $R_2=C_2H_5$), use of the commonly available 85% triethanol amine will almost certainly lead to a solid product, whereas the use of 99% triethanol amine will more likely than not lead to an initially liquid product.

We have further found that the addition of water to the product solution stablizes the product in liquid form. Water addition on the order of about 3 to 0.5 moles $H_2O$ per mole of zirconium has favorable stabilizing effects with the addition of 1 mole $H_2O$ per mole of zirconium being preferred. We suspect that the water results in the formation of a monohydrate of the product zirconate or perhaps even a monohydroxide.

The bisalkyl bis(trialkanol amine)zirconates of this invention are effective thickening agents for polysaccharides in aqueous solution, most notably polymers of guar gum and cellulose derivatives. Particularly preferred are hydratable polysaccharides such as galactomannan gums, and derivatives thereof, and cellulose derivatives. Examples of such compounds are guar gum, locust bean gum, karaya gum, sodium carboxymethylguar, hydroxyethylguar, sodium carboxymethylhydroxyethylguar, hydroxypropylguar, sodium carboxymethylhydroxymethylcellulose, sodium carboxymethylhydroxyethylcellulose and hydroxyethylcellulose. The hydroxyethylcellulose derivatives used as gelling agents should be those having from about 0.5 to about 10 moles of ethylene oxide per anhydroglucose unit. The most preferred gelling agent for use in accordance with the present invention is hydroxypropylguar (HPG).

Thickened aqueous solutions as described herein are particularly useful in the oil and gas industry as drilling muds, sands consolidations fluids and fracturing fluids.

The subject zirconates exhibit enhanced temperature stability when used to thicken galactomannan gums as compared to results with prior art thickening agents, such as the titanates. Thus when utilized as thickening agents for fluids used in resource recovery operations, zirconates according to the invention may be used in high temperature environments that would destabilize titanate thickening agents. This consideration takes on special significance as recovery operations, especially in the area of oil drilling, are directed to less-readily available sources of materials. The zirconates may, for example, be used to thicken galactomannan gums for use in fracturing oil wells that are drilled deeper and therefore present a hotter environment for fracturing. Although not yet verified, it is believed that the ΔH of the Zr—O bond being greater than that for the Ti—O bond accounts for this enhanced temperature stability, as well as the fact that the most common coordination numbers for zirconium and titanium are respectively 8 and 6.

EXAMPLE 1

771.4 gm of 99% triethanolamine were placed in a 3-neck, 3-liter r.b. flask. 1209.2 gm of tetra(n-propyl)zirconate (70% in n-propanol) were rapidly added while stirring the contents of the flask. After the heat of reaction had subsided, 46.6 gm of water were added to ensure that the compound remained a liquid at room temperature.

EXAMPLE 2

505.6 gm of 99% triethanolamine were added to 404.3 gm tetra(n-butyl)zirconate (80% in n-butanol). The temperature rose to 55° C., the mixture was allowed to cool to room temperature and 15.2 gm water were added.

EXAMPLE 3

To 404.3 gm tetra(n-butyl)zirconate (80% in n-butanol) were added 503.3 gm 99% triethanol amine. In the course of addition the solution temperature rose to 55° C. 15.2 gm $H_2O$ were then added to stabilize the product as a liquid. The resultant mixture was slightly hazy, the haze persisting even after filtration.

EXAMPLE 4

Example 3 was repeated using 85% triethanol amine. A precipitate formed after approximately one-half the amino alcohol has been added, resulting in a heterogeneous mixture in which the solid could not be re-dissolved.

EXAMPLE 5

0.4 gm. of the product of Example 1 added to 145 gm. of a stirred aqueous solution comprising hydrated hydroxypropylguar (HPG), an organic acid, sodium bicarbonate, a surfactant and a bactericide (this HPG formulation is commercially available as NWP-12 from NOWSCO, Inc., Houston, Tex. and was here used in a concentration of 50 lbs. per 1000 gal.). The viscosity of the HPG aqueous solution increased from an original value of 510 cp. to 177,000 cp. in about 30 to 45 seconds.

EXAMPLE 6

The product of Example 3 was found to thicken an aqueous solution of HPG. Thickening was determined to have occurred as of the onset of the Weisenberg effect, i.e., when the vortex of the stirred solution closed and the solution would begin to climb the stirrer shaft.

As suggested by the preceding material, the admixture of the amino alcohol and tetraalkoxy zirconium compound results in an exothermic reaction. The reaction temperature may vary from 0° to 100° C., with 25° to 75° C. being more preferred and about 25° to 60° C. being most preferred.

It will be understood that the specification and examples are illustrative but not limitative of the present invention and that other embodiments within the spirit and scope of the invention will suggest themselves to those skilled in the art.

What is claimed is:

1. A method for the preparation of a reaction product comprising a compound having the formula

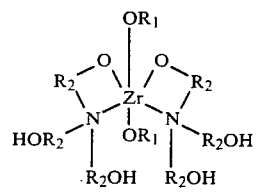

where $R_1$ and $R_2$ are individually selected from the group consisting of alkyl having from 1 to 8 carbon atoms, said method comprising the steps of admixing at least one tetraalkyl zirconate, of the form $Zr(OR_1)_4$, and at least one trialkanol amine, of the form $N(R_2OH)_3$, allowing the resultant reaction to proceed in the absence of applied heat and adding water to said reaction product in order to stabilize said reaction product in liquid form.

2. A method according to claim 1 wherein the molar ratio of trialkanol amine:zirconate as admixed is about 2:1.

3. A method according to claim 1 wherein about one mole of said water is added for each mole of zirconium in said admixture.

4. A method for the preparation of a reaction product comprising at least one bisalkyl bis(triethanol amine)zirconate, where the alkyl is selected from the group consisting of n-propyl and n-butyl, said method comprising the steps of admixing at least one tetraalkyl zirconate and triethanol amine, allowing the resultant reaction to proceed in the absence of applied heat and stabilizing said reaction product in liquid form by adding to the reaction product one mole of water for each mole of zirconium in said admixture.

5. A method according to claim 4, wherein the molar ratio of triethanol amine:zirconate as admixed is about 2:1.

6. The stabilized liquid form of the reaction product according to claim 1.

7. The stabilized liquid form of the reaction product according to claim 2.

8. The stabilized liquid form of the reaction product according to claim 3.

9. The stabilized liquid form of the reaction product according to claim 4.

10. The stabilized liquid form of the reaction product according to claim 5.